United States Patent
Shiratori et al.

(10) Patent No.: US 10,934,548 B2
(45) Date of Patent: Mar. 2, 2021

(54) WHEAT ALLERGEN-BINDING NUCLEIC ACID MOLECULE AND USE THEREOF

(71) Applicant: NEC Solution Innovators, Ltd., Tokyo (JP)

(72) Inventors: Tomoko Shiratori, Tokyo (JP); Naoto Kaneko, Tokyo (JP); Ikuo Shiratori, Tokyo (JP); Katsunori Horii, Tokyo (JP); Hirotaka Minagawa, Tokyo (JP); Jou Akitomi, Tokyo (JP); Yoshihito Yoshida, Tokyo (JP); Iwao Waga, Tokyo (JP)

(73) Assignee: NEC Solution Innovators, Ltd., Tokyo (JP)

( * ) Notice: Subject to any disclaimer, the term of this patent is extended or adjusted under 35 U.S.C. 154(b) by 377 days.

(21) Appl. No.: 15/776,142

(22) PCT Filed: Nov. 16, 2015

(86) PCT No.: PCT/JP2015/082139
§ 371 (c)(1),
(2) Date: May 15, 2018

(87) PCT Pub. No.: WO2017/085767
PCT Pub. Date: May 26, 2017

(65) Prior Publication Data
US 2020/0248181 A1 Aug. 6, 2020

(51) Int. Cl.
*C12N 15/11* (2006.01)
*C12N 15/115* (2010.01)
*C07K 14/415* (2006.01)
*C12Q 1/6883* (2018.01)

(52) U.S. Cl.
CPC .......... *C12N 15/115* (2013.01); *C07K 14/415* (2013.01); *C12Q 1/6883* (2013.01); *C12N 2310/16* (2013.01)

(58) Field of Classification Search
CPC ............... C12N 15/113; C12N 15/115; C12N 15/1048; C12N 2310/16
See application file for complete search history.

(56) References Cited

U.S. PATENT DOCUMENTS

| 2012/0202195 | A1* | 8/2012 | Waga | C12N 15/115 435/6.1 |
| 2015/0056720 | A1 | 2/2015 | Horii et al. | |
| 2016/0298117 | A1 | 10/2016 | Murata et al. | |

FOREIGN PATENT DOCUMENTS

| WO | WO 2012/113072 A1 | 8/2012 |
| WO | WO 2013/140629 A1 | 9/2013 |
| WO | WO 2013/140681 A1 | 9/2013 |
| WO | WO 2013/178844 A1 | 12/2013 |
| WO | WO-2013178844 A1 * | 12/2013 ......... C12N 15/115 |
| WO | WO 2015/083391 A1 | 6/2015 |
| WO | WO 2015/151350 A1 | 10/2015 |

OTHER PUBLICATIONS

James et al., Wheat alpha-amylase inhibitor: A second route of allergnic sensitization, Journal of Allergy and Clinical Immunology, vol. 99, pp. 239-244. (Year: 1997).*
Palosuo et al., Wheat omega-5 gliadin is a major allergen in children with immediate allergy to ingested wheat, Journal of Allergy and Clinical Immunology, vol. 108, pp. 634-638. (Year: 2001).*
Palacin et al., Wheat lipid transfer protein is a major allergen associated with baker's asthma, Journal of Allergy and Clinical Immunology, vol. 120, pp. 1132-1138. (Year: 2007).*
Evaldas Katilius et al., "Exploring the Sequence Space of a DNA Aptamer Using Microarrays," Nucleic Acids Research, Nov. 2, 2007, vol. 35, No. 22, pp. 7626-7635 (10 pages).
International Search Report corresponding to PCT/JP2015/082139, dated Feb. 9, 2016 (6 pages).
International Search Report and Written Opinion corresponding to PCT/JP2015/054535, dated Apr. 7, 2015 (12 pages).
Hiroshi Akiyama et al., "Inter-laboratory Evaluation Studies for Development of Notified ELISA Methods for Allergic Substances (Wheat)", Shokuhin Eiseigaku Zasshi (Food Hygiene and Safety Science), 2004, vol. 45, No. 3, pp. 128-134.
Luis Sorell et al., "An innovative sandwich ELISA system based on an antibody cocktail for gluten analysis", FEBS Letters, 1998, vol. 439, pp. 46-50.
Sonia Amaya-González et al., "Affinity of aptamers binding 33-mer gliadin peptide and gluten proteins: Influence of immobilization and labeling tags", Analytica Chimica Acta, 2015, vol. 873, pp. 63-70.
Sonia Amaya-González et al., "Aptamer Binding to Celiac Disease-Triggering Hydrophobic Proteins: A Sensitive Gluten Detection Approach", Analytical Chemistry, 2014, vol. 86, No. 5, pp. 2733-2739.
Sonia Amaya-González et al., "Sensitive gluten determination in gluten-free foods by an electrochemical aptamer-based assay", Analytical & Bioanalytical Chemistry, 2015, vol. 407, No. 20, pp. 6021-6029.
Alessandro Pinto et al., "Label-free detection of gliadin food allergen mediated by real-time apta-PCR", Analytical & Bioanalytical Chemistry, 2014, vol. 406, No. 2, pp. 515-524.
Sonia Amaya-González et al., "Aptamer-Based Analysis: A Promising Alternative for Food Safety Control", Sensors, 2013, vol. 13, No. 12, pp. 16292-16311.

(Continued)

*Primary Examiner* — Dana H Shin
(74) *Attorney, Agent, or Firm* — Wilmer Cutler Pickering Hale and Dorr LLP

(57) ABSTRACT

The present invention provides a novel nucleic acid molecule that can be used for detection of a wheat allergen. The wheat allergen-binding nucleic acid according to the present invention is characterized in that it binds to a wheat allergen with a dissociation constant of 20 nM or less, and preferably includes a polynucleotide consisting of either of base sequences of SEQ ID NOs: 1 and 2, for example.

8 Claims, 2 Drawing Sheets

Specification includes a Sequence Listing.

(56) References Cited

OTHER PUBLICATIONS

Tao Geng et al., "Detection of Gluten by Commercial Test Kits: Effects of Food Matrices and Extraction Procedures", American Chemical Society Symposium Series, vol. 1001, 2008, pp. 462-475.
Julie A. Nordlee et al., "Immunological Analysis of Food Allergens and Other Food Proteins", Food Technology, 1995, vol. 49, No. 2, pp. 129-132.
Camille L.A. Hamula et al., "Selection and analytical applications of aptamers", Trends in Analytical Chemistry, 2006, vol. 25, No. 7, pp. 681-691.

* cited by examiner

Aptamer 1
SEQ ID NO: 1

Aptamer 2
SEQ ID NO: 2

SEQUENCE LISTING

<160> NUMBER OF SEQ ID NOS: 2

<210> SEQ ID NO 1
<211> LENGTH: 30

```
<212> TYPE: DNA
<213> ORGANISM: Artificial Sequence
<220> FEATURE:
<223> OTHER INFORMATION: aptamer

<400> SEQUENCE: 1
gaggttgggt gggggaggca gcatgcggga                    30

<210> SEQ ID NO 2
<211> LENGTH: 18
<212> TYPE: DNA
<213> ORGANISM: Artificial Sequence
<220> FEATURE:
<223> OTHER INFORMATION: aptamer

<400> SEQUENCE: 2
gaggttgggt gggggagg                                 18
```

WHEAT ALLERGEN-BINDING NUCLEIC ACID MOLECULE AND USE THEREOF

CROSS-REFERENCE TO RELATED APPLICATIONS

This application is a national stage application of International Application No. PCT/JP2015/082139 entitled "WHEAT ALLERGEN-BINDING NUCLEIC ACID MOLECULE AND USE THEREOF," filed on Nov. 16, 2015. The disclosure which is hereby incorporated by reference in its entirety.

TECHNICAL FIELD

The present invention relates to a nucleic acid molecule that binds to a wheat allergen and use thereof.

SEQUENCE LISTING

The instant application contains a Sequence Listing which has been submitted electronically in ASCII format and is hereby incorporated by reference in its entirety. Said ASCII copy, created on Nov. 6, 2015 is named 3_20180426_Sequence_Listing_TF15095US.txt and is 585 bytes in size.

BACKGROUND ART

Wheat is a food people take frequently on a daily basis. In recent years, increase in patients with wheat allergy is seen as a problem. Wheat is used in a large variety of processed foods such as bread and noodles, for example. On this account, it is very important to check the presence of wheat as a raw material in processed foods, manufacturing lines thereof, etc.

Allergens, which are substances causing allergies, generally are proteins and degradation products thereof (peptides), and the mainstream approach for analyzing the allergens is to use antibodies against the allergens as antigens. As for wheat, gluten, which is a wheat protein, is known as an allergen, for example. As a method for analyzing gluten, there have been reported methods using ELISA (Non-Patent Documents 1 and 2).

However, antibodies are proteins and thus have a problem in stability. Thus, it is difficult to use an antibody in a test method that can be carried out easily at low cost.

CITATION LIST

Non-Patent Document(s)

Non-Patent Document 1: Hiroshi AKIYAMA, et al., "Inter-laboratory Evaluation Studies for Development of Notified ELISA Methods for Allergic Substances (Wheat)", Shokuhin Eiseigaku Zasshi (Food Hygiene and Safety Science), 2004, Vol. 45, No. 3, pp. 128-134

Non-Patent Document 2: Sorell, L. et al., "An innovative sandwich ELISA system based on an antibody cocktail for gluten analysis", FEBS Letters, 1998, Vol. 439, pp. 46-50

BRIEF SUMMARY OF THE INVENTION

With the foregoing in mind, it is an object of the present invention is to provide a novel nucleic acid molecule that can be used for detection of a wheat allergen.

The present invention provides a wheat allergen-binding nucleic acid molecule that binds to a wheat allergen with a dissociation constant of 20 nM or less.

The present invention also provides a wheat allergen analysis sensor including: the wheat allergen-binding nucleic acid molecule of the present invention.

The present invention also provides a wheat allergen analysis method including the step of: detecting a wheat allergen in a sample by causing the sample and the wheat allergen-binding nucleic acid molecule according to the present invention to come into contact with each other to bind the wheat allergen in the sample and the nucleic acid molecule.

The wheat allergen-binding nucleic acid molecule of the present invention can bind to a wheat allergen with the above-described dissociation constant. Thus, according to the wheat allergen-binding nucleic acid molecule of the present invention, a wheat allergen in a sample can be detected with high accuracy on the basis of the presence or absence of the binding with the wheat allergen, for example. Therefore, it can be said that the wheat allergen-binding nucleic acid molecule of the present invention is a very useful tool for the detection of a wheat allergen in the fields of food manufacturing, food management, food distribution, and the like, for example.

DETAILED DESCRIPTION OF THE INVENTION

Figure 1:
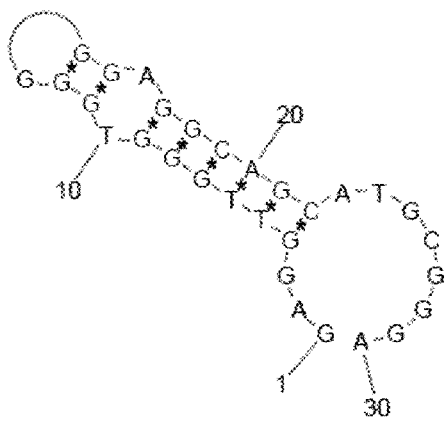
FIG. 1 is a schematic view showing examples of the predicted secondary structures of wheat allergen-binding nucleic acid molecules of the present invention.
Figure 1:
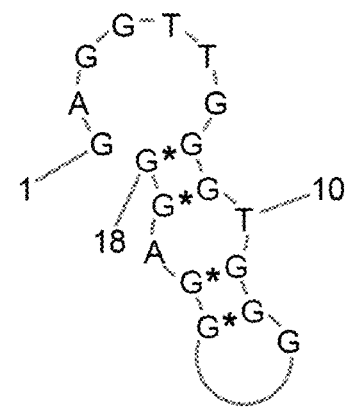

In the nucleic acid molecule of the present invention, the wheat allergen may be gluten or a subunit thereof, for example.

In the nucleic acid molecule of the present invention, the wheat allergen may be an undenatured allergen or a heat-denatured allergen, for example.

The nucleic acid molecule of the present invention may include, for example, at least one polynucleotide selected from the group consisting of the following polynucleotides (a) to (d).

(a) a polynucleotide consisting of either of base sequences of SEQ ID NOs: 1 and 2

(b) a polynucleotide that consists of a base sequence obtained by deletion, substitution, insertion, and/or addition of one or more bases in either of the base sequences of the polynucleotide (a) and binds to the wheat allergen (c) a polynucleotide that consists of a base sequence with a sequence identity of at least 80% to either of the base sequences of the polynucleotide (a) and binds to the wheat allergen (d) a polynucleotide that consists of a base sequence complementary to a polynucleotide hybridizing to either of the base sequences of the polynucleotide (a) under stringent conditions and binds to the wheat allergen In the nucleic acid molecule of the present invention, the polynucleotide may be a DNA, for example.

The analysis sensor of the present invention may further include a nucleic acid molecule that forms a G-quartet structure, for example.

In the analysis sensor of the present invention, the nucleic acid molecule that forms a G-quartet structure may be a DNAzyme or an RNAzyme, for example.

The analysis sensor of the present invention further may include porphyrin, for example.

In the analysis method of the present invention, the sample may be at least one selected from the group consisting of foods, food ingredients, and food additives, for example.

(1) Wheat Allergen-Binding Nucleic Acid Molecule

As described above, the wheat allergen-binding nucleic acid molecule of the present invention is characterized in that it binds to a wheat allergen with a dissociation constant of 20 nM or less.

The nucleic acid molecule of the present invention binds to, for example, gluten (a major allergen of wheat), the subunit thereof, or a domain thereof.

The wheat allergen may be an undenatured allergen without denaturation by heating or a denatured allergen with denaturation by heating, for example. The nucleic acid molecule of the present invention can bind to both undenatured and denatured allergens, for example.

The nucleic acid molecule of the present invention binds to the wheat allergen with a dissociation constant of 20 nM or less, or 15 nM or less, for example. The minimum detectable concentration of the wheat allergen by the nucleic acid molecule of the present invention is 250 nM or 125 nM, for example.

The nucleic acid molecule of the present invention binds to the gluten with a dissociation constant of 20 nM or less, or 15 nM or less, for example. The minimum detectable concentration of the gluten by the nucleic acid molecule of the present invention is 250 nM or 125 nM, for example.

The binding between the nucleic acid molecule of the present invention and the wheat allergen can be determined by surface plasmon resonance molecular interaction (SPR; Surface Plasmon Resonance) analysis, for example. The analysis can be performed using ProteON (trade name, BioRad), for example.

Specific examples of the wheat allergen-binding nucleic acid molecule of the present invention are shown below. The nucleic acid molecule of the present invention is, for example, a nucleic acid molecule including the following polynucleotide (a). In the present invention, the nucleic acid molecule including the polynucleotide (a) encompasses, for example, nucleic acid molecules including at least one polynucleotide selected from the group consisting of polynucleotides (b) to (d).

(a) a polynucleotide consisting of either of base sequences of SEQ ID NOs: 1 and 2
(b) a polynucleotide that consists of a base sequence obtained by deletion, substitution, insertion, and/or addition of one or more bases in either of the base sequences of the polynucleotide (a) and binds to the wheat allergen
(c) a polynucleotide that consists of a base sequence with a sequence identity of at least 80% to either of the base sequences of the polynucleotide (a) and binds to the wheat allergen
(d) a polynucleotide that consists of a base sequence complementary to a polynucleotide hybridizing to either of the base sequences of the polynucleotide (a) under stringent conditions and binds to the wheat allergen In the nucleic acid molecule of the present invention, the building blocks of the polynucleotide are, for example, nucleotide residues, examples of which include deoxyribonucleotide residues and ribonucleotide residues. The polynucleotide is, for example, DNA consisting of deoxyribonucleotide residues or DNA including a deoxyribonucleotide residue(s) and a ribonucleotide residue(s), and the polynucleotide may further include a non-nucleotide residue(s), as described below. The wheat allergen-binding nucleic acid molecule of the present invention also is referred to as "DNA aptamer" hereinafter, for example.

The nucleic acid molecule according to the present invention may consist of any of the polynucleotides (a) to (d) or may include any of the polynucleotides (a) to (d), for example. In the latter case, the nucleic acid molecule of the present invention may include, for example, two or more polynucleotides selected from the polynucleotides (a) to (d), as described below. The two or more polynucleotides may be the polynucleotides with the same sequence or different sequences. Also, in the latter case, the nucleic acid molecule of the present invention further may include a linker(s) and/or an additional sequence(s), for example.

The polynucleotide (a) is a polynucleotide consisting of either of the base sequences of SEQ ID NOs: 1 and 2.

TABLE 1

Aptamer 1 (SEQ ID No: 1)
GAGGTTGGGTGGGGGAGGCAGCATGCGGGA

Aptamer 2 (SEQ ID No: 2)
GAGGTTGGGTGGGGGAGG

SEQ ID NO: 2 is a truncated sequence of SEQ ID NO: 1. In Table 1 above, the underlined region in SEQ ID NO: 1 corresponds to the base sequence of SEQ ID NO: 2. FIG. 1 shows predicted secondary structures of polynucleotides consisting of the base sequences of SEQ ID NOs: 1 and 2, respectively. It is to be noted, however, that the present invention is not limited thereto.

Regarding the polynucleotide (b), the term "one or more" is not limited as long as, for example, it is in the range where the polynucleotide (b) binds to the wheat allergen. The number of the "one or more" bases in either of the base sequences of the polynucleotide (a) are 1 to 10, 1 to 7, 1 to 5, 1 to 3, or 1 or 2, for example. In the present invention, the numerical range regarding the number of bases, sequences, or the like discloses, for example, all the positive integers falling within that range. That is, for example, the description "one to five bases" discloses all of "one, two, three, four, and five bases" (the same applies hereinafter).

Regarding the polynucleotide (c), the "sequence identity" is not limited as long as, for example, it is in the range where the polynucleotide (c) binds to the wheat allergen. The sequence identity is, for example, at least 80%, at least 85%, at least 90%, at least 95%, at least 96%, at least 97%, at least 98%, or at least 99%. The sequence identity can be calculated with analysis software such as BLAST or FASTA using default parameters, for example (the same applies hereinafter).

Regarding the polynucleotide (d), the "polynucleotide hybridizing to" is, for example, a polynucleotide perfectly or partially complementary to the polynucleotide (a). The hybridization can be detected by various types of hybridization assay, for example. The hybridization assay is not particularly limited, and for example, a method described in "Molecular Cloning: A Laboratory Manual 2nd Ed." edited by Sambrook et al. (Cold Spring Harbor Laboratory Press [1989]) or the like can be employed.

Regarding the polynucleotide (d), the "stringent conditions" may be any of low stringency conditions, medium stringency conditions, and high stringency conditions, for example. The "low stringency conditions" are, for example, conditions where 5×SSC, 5×Denhardt's solution, 0.5% SDS, and 50% formamide are used at 32° C. The "medium stringency conditions" are, for example, conditions where 5×SSC, 5×Denhardt's solution, 0.5% SDS, and 50% formamide are used at 42° C. The "high stringency conditions" are, for example, conditions where 5×SSC, 5×Denhardt's solution, 0.5% SDS, and 50% formamide, are used at 50° C. Those skilled in the art can set the degree of stringency by, for example, setting the conditions such as the temperature, the salt concentration, the concentration and length of a probe, the ionic strength, the time, etc. as appropriate. As the "stringent conditions", it is also possible to employ conditions described in the above-described "Molecular Cloning: A Laboratory Manual 2nd Ed." edited by Sambrook et al. (Cold Spring Harbor Laboratory Press [1989]) or the like, for example.

The nucleic acid molecule according to the present invention may include, for example, any one sequence selected from the polynucleotides (a) to (d), or a plurality of sequences selected from the polynucleotides (a) to (d). In the latter case, it is preferable that the plurality of polynucleotide sequences are linked to each other to form a single-stranded polynucleotide. The plurality of polynucleotide sequences may be linked to each other directly, or may be linked to each other indirectly with a linker, for example. It is preferable that the polynucleotide sequences are linked to each other directly or indirectly at their ends. The plurality of polynucleotide sequences may be the same or different from each other, for example. Preferably, the plurality of polynucleotide sequences are the same, for example. When the nucleic acid molecule of the present invention includes the plurality of polynucleotide sequences, the number of the sequences is not particularly limited. The number of the sequences is, for example, 2 or more, 2 to 20, 2 to 10, or 2 or 3.

The linker is not particularly limited. The length of the linker is not particularly limited, and is, for example, 1- to 200-mer, 1- to 20-mer, 3- to 12-mer, or 5- to 9-mer. The building blocks of the linker are, for example, nucleotide residues, examples of which include deoxyribonucleotide residues and ribonucleotide residues. The linker is not particularly limited, and examples thereof include polynucleotides such as DNA consisting of deoxyribonucleotide residues and DNA including a ribonucleotide residue(s). Specific examples of the linker include polydeoxythymine (poly(dT)), polydeoxyadenine (poly(dA)), and poly(dA-dT) having a repetitive sequence composed of A and T. Preferably, the linker is poly(dT) or poly(dA-dT).

In the nucleic acid molecule of the present invention, the polynucleotide preferably is a single-stranded polynucleotide. It is preferable that the single-stranded polynucleotide can form a stem structure and a loop structure by self-annealing, for example. It is preferable that the polynucleotide can form a stem-loop structure, an internal loop structure, and/or a bulge structure, for example.

The nucleic acid molecule of the present invention may be a double strand, for example. When the nucleic acid molecule is a double strand, for example, one of single-stranded polynucleotides includes any of the polynucleotides (a) to (d), and the other single-stranded polynucleotide is not limited. The other single-stranded polynucleotide may be, for example, a polynucleotide including a base sequence complementary to any of the polynucleotides (a) to (d). When the nucleic acid molecule of the present invention is a double strand, it is preferable to dissociate the double strand to single-stranded polynucleotides by denaturation or the like before use, for example. Also, it is preferable that the dissociated single-stranded polynucleotide including any of the polynucleotides (a) to (d) is forming a stem structure and a loop structure as described above, for example.

In the present invention, the expression "can form a stem structure and a loop structure (and grammatical variations thereof)" encompasses that, for example, a stem structure and a loop structure are formed actually, and also, even if a stem structure and a loop structure are not formed, they can be formed depending on conditions. The expression "can form a stem structure and a loop structure (and grammatical variations thereof)" encompasses, for example, both the cases where the formation thereof has been confirmed through an experiment and where the formation thereof is predicted through simulation using a computer or the like.

The building blocks of the nucleic acid molecule of the present invention are, for example, nucleotide residues. Examples of the nucleotide residues include deoxyribonucleotide residues and ribonucleotide residues. Examples of the nucleic acid molecule of the present invention include DNA consisting of deoxyribonucleotide residues only and DNA including one or more ribonucleotide residues. In the latter case, "one or more" is not particularly limited. For example, the number of the ribonucleotide residues in the polynucleotide is, for example, 1 to 91, 1 to 30, 1 to 15, 1 to 7, 1 to 3, or 1 or 2.

The polynucleotide may include a modified base(s). The modified base is not particularly limited, and may be, for example, a modified natural base (non-artificial base), which preferably has a similar function to the natural base. The natural base is not particularly limited, and may be, for example, a purine base with a purine skeleton or a pyrimidine base with a pyrimidine skeleton. The purine base is not particularly limited, and examples thereof include adenine (a) and guanine (g). The pyrimidine base is not particularly limited, and examples thereof include cytosine (c), thymine (t), and uracil (u). The modified site in the base is not particularly limited. When the base is a purine base, the modified site in the purine base may be, for example, the 7-position or the 8-position in the purine skeleton. When the base is a pyrimidine base, the modified site in the pyrimidine base may be, for example, the 5-position or the 6-position in the pyrimidine skeleton. When the pyrimidine skeleton has "=O" bound to the carbon at the 4-position and a group that is not "—CH3" or "—H" bound to the carbon at the 5-position, the modified base can be referred to as modified uracil or modified thymine.

The modifying group in the modified base is not particularly limited, and may be, for example, a methyl group, a fluoro group, an amino group, a thio group, a benzylaminocarbonyl group represented by the following formula (1), a tryptaminocarbonyl group represented by the following formula (2), or an isobutylaminocarbonyl group.

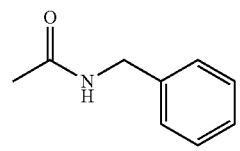

(1)

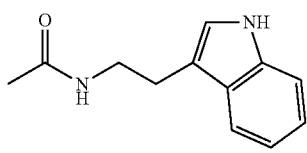
(2)

The modified base is not particularly limited, and examples thereof include: modified adenine, which is adenine with modification; modified thymine, which is thymine with modification; modified guanine, which is guanine with modification; modified cytosine, which is cytosine with modification; and modified uracil, which is uracil with modification. Among them, the modified thymine, the modified uracil, and the modified cytosine are preferable.

Specific examples of the modified adenine include 7'-deazaadenine.

Specific examples of the modified guanine include 7'-deazaguanine.

Specific examples of the modified cytosine include 5'-methylcytosine (5-Me-dC).

Specific examples of the modified thymine include 5'-benzylaminocarbonyl thymine, 5'-tryptaminocarbonyl thymine, and 5'-isobutylaminocarbonyl thymine.

Specific examples of the modified uracil include 5'-benzylaminocarbonyl uracil (BndU), 5'-tryptaminocarbonyl uracil (TrpdU), and 5'-isobutylaminocarbonyl uracil. Each modified uracil given above as examples also can be referred to as modified thymine.

The polynucleotide may include, for example, only one type or two or more types of the modified bases.

The nucleic acid molecule of the present invention may include a modified nucleotide(s), for example. The modified nucleotide may be a nucleotide having the above-described modified base, a nucleotide having a modified sugar obtained through modification of a sugar residue, or a nucleotide having the modified base and the modified sugar.

The sugar residue is not particularly limited, and may be a deoxyribose residue or a ribose residue, for example. The modified site in the sugar residue is not particularly limited, and may be, for example, the 2'-position or the 4'-position in the sugar residue. Either one or both of the 2'-position and the 4'-position may be modified. Examples of a modifying group in the modified sugar include methyl groups, fluoro groups, amino groups, and thio groups.

In the case where the base in the modified nucleotide residue is a pyrimidine base, it is preferable that the 2'-position and/or the 4'-position in the sugar residue is modified, for example. Specific examples of the modified nucleotide residue include modified nucleotide residues with the 2'-position in the deoxyribose residue or ribose residue being modified, such as a 2'-methylated-uracil nucleotide residue, 2'-methylated-cytosine nucleotide residue, 2'-fluorinated-uracil nucleotide residue, 2'-fluorinated-cytosine nucleotide residue, 2'-aminated-uracil nucleotide residue, 2'-aminated-cytosine nucleotide residue, 2'-thiated-uracil nucleotide residue, and 2'-thiated-cytosine nucleotide residue.

The number of the modified nucleotides is not particularly limited. For example, the number of the modified nucleotides in the polynucleotide is, for example, 1 to 100, 1 to 90, 1 to 80, or 1 to 70. Also, the number of the modified nucleotides in the full-length nucleic acid molecule including the polynucleotide is not particularly limited, and is, for example, 1 to 91, 1 to 78, or in the numerical ranges given above as examples of the number of the modified nucleotides in the polynucleotide.

The nucleic acid molecule of the present invention may include, for example, one or more artificial nucleic acid monomer residues. The term "one or more" is not particularly limited, and may be, for example, 1 to 100, 1 to 50, 1 to 30, or 1 to 10 in the polynucleotide, for example. Examples of the artificial nucleic acid monomer residue include peptide nucleic acids (PNAs), locked nucleic acids (LNAs), and 2'-O,4'-C-ethylenebridged nucleic acids (ENAs). The nucleic acid in the monomer residue is the same as described above, for example.

It is preferable that the nucleic acid molecule of the present invention is resistant to nuclease, for example. In order to allow the nucleic acid molecule to have nuclease resistance, it is preferable that the nucleic acid molecule of the present invention includes the modified nucleotide residue(s) and/or the artificial nucleic acid monomer residue(s), for example. Also, in order to allow the nucleic acid molecule to have nuclease resistance, the nucleic acid molecule of the present invention may have polyethylene glycol (PEG) of several tens of kDa, deoxythymidine, or the like bound to, e.g., the 5' end or the 3' end thereof.

The nucleic acid molecule of the present invention may further include an additional sequence, for example. Preferably, the additional sequence is bound to at least one of the 5' end and the 3' end, more preferably to the 3' end of the nucleic acid molecule, for example. The additional sequence is not particularly limited. The length of the additional sequence is not particularly limited, and is, for example, 1- to 200-mer, 1- to 50-mer, 1- to 25-mer, or 18- to 24-mer. The building blocks of the additional sequence are, for example, nucleotide residues, examples of which include deoxyribonucleotide residues and ribonucleotide residues. The additional sequence is not particularly limited, and examples thereof include polynucleotides such as DNA consisting of deoxyribonucleotide residues and DNA including a ribonucleotide residue(s). Specific examples of the additional sequence include poly(dT) and poly(dA).

The nucleic acid molecule of the present invention can be used in the state where it is immobilized on a carrier, for example. It is preferable to immobilize either the 5' end or the 3' end, more preferably the 3' end of the nucleic acid molecule of the present invention, for example. When the nucleic acid molecule of the present invention is immobilized, the nucleic acid molecule may be immobilized either directly or indirectly to the carrier, for example. In the latter case, it is preferable to immobilize the nucleic acid molecule via the additional sequence, for example.

The nucleic acid molecule of the present invention may further include a labeling substance, for example. The labeling substance preferably is bound to at least one of the 5' end and the 3' end, more preferably to the 5' end of the nucleic acid molecule, for example. The labeling substance is not particularly limited, and reference can be made to an explanation thereon to be provided below, for example.

The method for producing the nucleic acid molecule of the present invention is not particularly limited. For example, the nucleic acid molecule of the present invention can be synthesized by known methods such as: nucleic acid synthesis utilizing chemical synthesis methods; and genetic engineering procedures. The nucleic acid molecule of the present invention also can be obtained by a so-called SELEX method, for example. In this case, a target preferably is gluten, which is a wheat allergen.

The nucleic acid molecule of the present invention exhibits binding properties to the wheat allergen, as described above. Thus, use of the nucleic acid molecule of the present invention is not particularly limited, as long as it is the use utilizing the binding properties of the nucleic acid molecule to the wheat allergen. The nucleic acid molecule of the present invention can be used in various methods as an alternative to, e.g., an antibody against the wheat allergen.

(2) Wheat Allergen Analysis Sensor

As described above, the wheat allergen analysis sensor of the present invention is characterized in that it includes the wheat allergen-binding nucleic acid molecule according to the present invention. It is only required that the sensor of the present invention includes the wheat allergen-binding nucleic acid molecule of the present invention, and other configurations are by no means limited.

The sensor of the present invention may further include a binding detection nucleic acid molecule for detecting the binding between the wheat allergen-binding nucleic acid molecule and the wheat allergen. The binding detection nucleic acid molecule is active in the state where the wheat allergen is bound to the wheat allergen-binding nucleic acid molecule and inactive in the state where the wheat allergen is not bound to the wheat allergen-binding nucleic acid molecule, for example. When the sensor of the present invention includes the binding detection nucleic acid molecule, it is possible to check the presence or absence of the binding of the wheat allergen to the wheat allergen-binding nucleic acid molecule depending on whether the binding detection nucleic acid molecule is active or inactive, whereby the presence or absence of the wheat allergen can be analyzed.

The binding detection nucleic acid molecule may be a nucleic acid molecule that forms a G-quartet structure, for example. The nucleic acid molecule that forms the G-quartet structure is active in the state where it has formed the G-quartet structure and inactive in the state where it does not form the G-quartet structure, for example.

The nucleic acid molecule that forms a G-quartet structure is, for example, a DNAzyme or an RNAzyme, and preferably is a DNAzyme.

The active DNAzyme that has formed the G-quartet structure exhibits peroxidase-like activity catalyzing a redox reaction, for example. Thus, when the sensor of the present invention includes a DNAzyme, it is possible to analyze the presence or absence or the amount of the binding of the wheat allergen to the wheat allergen-binding nucleic acid molecule by detecting the catalytic activity of the DNAzyme.

In this case, it is preferable that the sensor of the present invention also includes a porphyrin, for example. The porphyrin is not particularly limited, and examples thereof include unsubstituted porphyrins and derivatives thereof. Examples of the derivatives include substituted porphyrins and metal porphyrins that have formed complexes with metal elements. Examples of the substituted porphyrins include N-methylmesoporphyrin. Examples of the metal porphyrins include hemin, which is a trivalent iron complex. For example, the porphyrin preferably is the metal porphyrin, more preferably hemin.

An active DNAzyme that has formed a G-quartet structure generates fluorescence by forming a complex with a porphyrin, for example. Thus, when the sensor of the present invention includes a DNAzyme, it is possible to analyze the presence or absence or the amount of the binding of the wheat allergen to the wheat allergen-binding nucleic acid molecule by allowing the DNAzyme to be present with a porphyrin and detecting fluorescence generated by the formation of a complex of the DNAzyme with the porphyrin.

The porphyrin is not particularly limited, and preferably is N-methylmesoporphyrin (NMM), Zn-DIGP, ZnPP9, or TMPyP, for example.

The sensor of the present invention may further include a labeling substance, for example. The labeling substance preferably is bound to at least one of the 5' end and the 3' end, more preferably to the 5' end of the nucleic acid molecule, for example. The labeling substance is not particularly limited, and may be, for example, a fluorescent substance, a dye, an isotope, an enzyme, or the like. Examples of the fluorescent substance include fluorophores such as pyrene, TAMRA, fluorescein, Cy3 dye, Cy5 dye, FAM dye, rhodamine dye, Texas Red dye, JOE, MAX, HEX, and TYE. Examples of the dye include Alexa dyes such as Alexa 488 and Alexa 647. Examples of the enzyme include luciferase, alkaline phosphatase, peroxidase, β-galactosidase, and glucuronidase.

The labeling substance may be linked to the nucleic acid molecule directly, or indirectly via a linker, for example. The linker is not particularly limited, and examples thereof include those given above as examples of the linker.

(3) Analysis Method

As described above, the analysis method of the present invention is a method for analyzing a wheat allergen, including the step of: detecting a wheat allergen in a sample by causing the sample and the wheat allergen-binding nucleic acid molecule according to the present invention to come into contact with each other to bind the wheat allergen in the sample and the nucleic acid molecule. The analysis method of the present invention is characterized in that it uses the nucleic acid molecule of the present invention, and other steps, conditions, etc. are not particularly limited. In the analysis method of the present invention, the wheat allergen analysis sensor according to the present invention may be used as the nucleic acid molecule according to the present invention.

The nucleic acid molecule of the present invention specifically binds to a wheat allergen. Thus, according to the present invention, it is possible to specifically detect a wheat allergen in a sample by detecting the binding between the wheat allergen and the nucleic acid molecule, for example. Specifically, for example, since the present invention can analyze the presence or absence or the amount of a wheat allergen in a sample, it can be said that the present invention can perform qualitative or quantitative analysis of the wheat allergen.

In the present invention, the sample is not particularly limited. Examples of the sample include foods, food ingredients, and food additives. Examples of the sample also include substances attached to food-processing factories, kitchens, etc. and liquids obtained after washing the food-processing factories, kitchens, etc.

The sample may be a liquid sample or a solid sample, for example. The sample preferably is a liquid sample from the viewpoint of ease of handling because the liquid sample can be brought into contact with the nucleic acid molecule more easily, for example. In the case of the solid sample, a mixed solution, a liquid extract, a solution, or the like of the solid sample prepared using a solvent may be used, for example. The solvent is not particularly limited, and may be water, physiological saline, or a buffer solution, for example.

The above-described detection step includes, for example: a contact step of causing the sample and the nucleic acid molecule to come into contact with each other to bind the wheat allergen in the sample and the nucleic acid molecule; and a binding detection step of detecting the binding between the wheat allergen and the nucleic acid molecule. The detection step may further include, for example, the step of analyzing the presence or absence or the amount of the wheat allergen in the sample on the basis of the result obtained in the binding detection step.

In the contact step, the method for causing the sample and the nucleic acid molecule to come into contact with each other is not particularly limited. The contact between the sample and the nucleic acid molecule preferably is achieved in a liquid, for example. The liquid is not particularly limited, and may be water, physiological saline, or a buffer solution, for example.

In the contact step, the conditions under which the contact between the sample and the nucleic acid molecule is caused are not particularly limited. The contact temperature is, for example, 4° C. to 37° C., or 18° C. to 25° C. The contact time is, for example, 10 to 120 minutes, or 30 to 60 minutes.

In the contact step, the nucleic acid molecule may be an immobilized nucleic acid molecule immobilized on a carrier or an unimmobilized nucleic acid molecule in a free state, for example. In the latter case, for example, the nucleic acid molecule is brought into contact with the sample in a container. The nucleic acid molecule preferably is the immobilized nucleic acid molecule from the viewpoint of favorable handleability, for example. The carrier is not particularly limited, and may be a substrate, beads, or a container, for example. The container may be a microplate or a tube, for example. The immobilization of the nucleic acid molecule is as described above, for example.

The binding detection step is the step of detecting the binding between the wheat allergen in the sample and the nucleic acid molecule, as described above. By detecting the presence or absence of the binding between the wheat allergen and the nucleic acid molecule, it is possible to analyze the presence or absence of the wheat allergen in the sample (qualitative analysis), for example. Also, by detecting the degree of the binding (the amount of the binding) between the wheat allergen and the nucleic acid molecule, it is possible to analyze the amount of the wheat allergen in the sample (quantitative analysis), for example.

In the case where the binding between the wheat allergen and the nucleic acid molecule cannot be detected, it can be determined that no wheat allergen is present in the sample. In the case where the binding is detected, it can be determined that the wheat allergen is present in the sample.

The method for analyzing the binding between the wheat allergen and the nucleic acid molecule is not particularly limited. A conventionally known method for detecting the binding between substances may be employed as the method, for example, and specific examples of the method include the above-described SPR and fluorescence polarization. Detection of the binding may be detection of a complex of the wheat allergen with the nucleic acid molecule, for example.

Detection of the binding between the wheat allergen and the nucleic acid molecule by the fluorescence polarization can be carried out in the following manner, for example.

The fluorescence polarization is a measurement method generally based on the properties of a labeling substance that, when the labeling substance is irradiated with polarized excitation light, fluorescence emitted from the labeling substance exhibits different polarization degrees depending on the molecular weight of a molecule labeled with the labeling substance. In the present invention, the binding between the wheat allergen and the nucleic acid molecule can be detected by the fluorescence polarization by, for example, using the nucleic acid molecule labeled with the labeling substance (the labeled nucleic acid molecule). Specifically, when the labeled nucleic acid molecule in the state where a wheat allergen is not bound thereto is compared with the labeled nucleic acid molecule in the state where the wheat allergen is bound thereto, the former has a relatively small molecular weight and thus exhibits a relatively low polarization degree, whereas the latter has a relatively large molecular weight and thus exhibits a relatively high polarization degree. Thus, the binding between the wheat allergen and the labeled nucleic acid molecule can be detected by, for example, comparing the polarization degree of the labeled nucleic acid molecule before the contact with the sample with the polarization degree of the labeled nucleic acid molecule after the contact with the sample. Further, the binding between the wheat allergen and the labeled nucleic acid molecule also can be detected by, for example, evaluating the polarization degree of the labeled nucleic acid molecule after the contact with the sample using, as a reference value for evaluation, at least one of the polarization degree of the labeled nucleic acid molecule not bound to the wheat allergen and the polarization degree of the labeled nucleic acid molecule bound to the wheat allergen.

According to the fluorescence polarization, the nucleic acid molecule of the present invention can be used easily as a sensor by merely labeling it with the labeling substance, for example. The detection wavelength for the labeling substance varies depending on the type of the labeling substance. Thus, for example, by selecting the labeling substance depending on the type of a sample, it is possible to reduce the influence by fluorescence derived from the sample.

The labeled nucleic acid molecule is not limited as long as, for example, the nucleic acid molecule of the present invention is labeled with the labeling substance, and the method for labeling the nucleic acid molecule is not particularly limited.

The labeled nucleic acid molecule may be configured so that, for example, the labeling substance is linked to the nucleic acid molecule of the present invention. Regarding this configuration, reference can be made to the above description, for example, and the labeling substance may be linked to the nucleic acid molecule of the present invention directly, or indirectly via a linker or the like as described above. The length of the linker is not particularly limited, and is, for example, 0- to 10-mer, 0- to 7-mer, or 0- to 5-mer. The labeling substance may be linked to any site in the nucleic acid molecule of the present invention, for example. Specific examples of the site include the 5' end and the 3' end of the nucleic acid molecule. The labeling substance may be linked to both the ends, or may be linked to either one of the ends, preferably to the 5' end.

Other examples of the labeled nucleic acid molecule include a hybrid molecule including the nucleic acid molecule of the present invention and a complementary strand that is complementary to the nucleic acid molecule and has a labeling substance linked thereto (hereinafter this complementary strand also is referred to as "labeled complementary strand"), in which the nucleic acid molecule and the labeled complementary strand are hybridized to each other.

It is only required that the complementary strand has a sequence complementary to a part of the nucleic acid molecule of the present invention, for example. The complementary strand may consist of the complementary sequence or may include the complementary sequence. The complementary strand may be complementary to any region in the nucleic acid molecule of the present invention, and preferably is complementary to a 5' end region or a 3' end region. For example, it is preferable that the nucleic acid molecule of the present invention has a linker at the 5' end or 3' end thereof and the complementary sequence is complementary to the linker. The length of the linker is not particularly limited, and is, for example, 10- to 30-mer, 15- to 25-mer, or 18- to 24-mer. The length of the complementary strand is not particularly limited, and is, for example, 10- to 30-mer, 15- to 25-mer, or 18- to 24-mer.

In the labeled complementary strand, the labeling substance may be linked to any site in the complementary strand, for example. Specific examples of the site include the 5' end and the 3' end of the complementary strand. The labeling substance may be linked to both the ends, or may be linked to either one of the ends. When the labeled complementary strand is complementary to a 3' end region in the nucleic acid molecule of the present invention, the labeling substance preferably is linked to the 5' end of the complementary strand. When the labeled complementary strand is complementary to a 5' end region of the nucleic acid molecule of the present invention, the labeling substance preferably is linked to the 3' end of the complementary strand.

The labeling substance is not particularly limited, and examples thereof include those given above as examples of the labeling substance. Among them, the fluorescent substances and the dyes are preferable.

When the fluorescence polarization is employed, the analysis method of the present invention preferably includes, for example: a contact step of causing the sample and the labeled nucleic acid molecule to come into contact with each other to bind the wheat allergen in the sample to the labeled nucleic acid molecule; a measurement step of measuring the polarization degree of the labeled nucleic acid molecule by irradiating the labeled nucleic acid molecule with polarized excitation light; and a detection step of detecting the binding between the wheat allergen and the labeled nucleic acid molecule by comparing the result of the measurement obtained in the measurement step with a reference value for evaluation.

In the measurement step, the wavelength of the polarized excitation light and the detection wavelength for the polarization degree are not particularly limited, and can be set as appropriate depending on the type of the labeling substance, for example. As a specific example, when the labeling substance is Alexa 647, the wavelength of the polarized excitation light is, for example, 620 to 680 nm, and the detection wavelength for the polarization degree is, for example, 660 to 800 nm. The irradiation time with the polarized excitation light is not particularly limited, and may be, for example, 1 nanosecond to 5 nanoseconds.

In the detection step, the reference value for evaluation may be determined previously, or may be determined for each measurement, for example. As the reference value for evaluation, it is possible to set, for example, a reference value for the state where the wheat allergen is not bound to labeled nucleic acid molecule or a reference value for the state where the wheat allergen is bound to labeled nucleic acid molecule. The former reference value is, for example, the polarization degree of the labeled nucleic acid molecule alone without the wheat allergen bound thereto. The latter reference value is, for example, the polarization degree of the labeled nucleic acid molecule with the wheat allergen bound thereto.

In the case where the former reference value is used, it can be determined that the wheat allergen is present when the measured value in the measurement step is higher than the reference value, for example. Also, as the measured value becomes relatively higher than the reference value, it can be determined that a relatively larger amount of the wheat allergen is present. On the other hand, when the measured value in the measurement step is substantially equal to or lower than the reference value, it can be determined that the wheat allergen is not present. The former reference value may be, for example, the polarization degree of the labeled nucleic acid molecule before the contact step.

In the case where the latter reference value is used, it can be determined that the wheat allergen is not present when the measured value in the measurement step is lower than the reference value, for example. On the other hand, when the measured value in the measurement step is substantially equal to or higher than the reference value, it can be determined that the wheat allergen is present. Also, as the measured value becomes relatively higher than the reference value, it can be determined that a relatively larger amount of the wheat allergen is present.

The reference value may be the correlation between the amount of the wheat allergen and the polarization degree. For example, a correlation equation representing the correlation can be obtained by causing a wheat allergen at a plurality of known concentrations and the predetermined amount of the labeled nucleic acid molecule to come into contact with each other and measuring the polarization degree of the labeled nucleic acid molecule bound to the wheat allergen at each concentration. Then, using the correlation equation and the measured value in the measurement step, it is possible to determine the amount of the wheat allergen in the sample.

When the wheat allergen analysis sensor of the present invention is used as the nucleic acid molecule of the present invention, the wheat allergen can be detected by, for example, detecting a redox reaction or detecting the generation of fluorescence.

In the case where the sensor of the present invention includes a DNAzyme that forms a G-quartet structure as the binding detection nucleic acid molecule as described above, the DNAzyme forms the G-quartet structure when the wheat allergen binds to the wheat allergen-binding nucleic acid molecule and thus turns to an active DNAzyme exhibiting a peroxidase-like activity catalyzing a redox reaction. Thus, by detecting the redox reaction, it is possible to detect the binding of the wheat allergen to the wheat allergen-binding nucleic acid molecule. In this case, it is preferable to use a substrate for the redox reaction in combination, for example.

The substrate is not particularly limited, and examples thereof include 3,3',5,5'-Tetramethylbenzidine (TMB), 1,2-Phenylenediamine (OPD), 2,2'-Azinobis (3-ethylbenzothiazoline-6-sulfonic Acid) Ammonium Salt (ABTS), 3,3'-Diaminobenzidine (DAB), 3,3'-Diaminobenzidine Tetrahydrochloride Hydrate (DAB4HCl), 3-Amino-9-ethylcarbazole (AEC), 4-Chloro-1-naphthol (4ClN), 2,4,6-Tribromo-3-hydroxybenzoic Acid, 2,4-Dichlorophenol, 4-Aminoantipyrine, 4-Aminoantipyrine Hydrochloride, and luminol.

Also, in the case where the sensor of the present invention includes a DNAzyme that forms a G-quartet structure as the binding detection nucleic acid molecule, the DNAzyme forms the G-quartet structure upon binding of the wheat allergen to the wheat allergen-binding nucleic acid molecule, thereby forming a complex with a porphyrin to generate fluorescence. Thus, by detecting the fluorescence, it is possible to detect the binding of the wheat allergen to the wheat allergen-binding nucleic acid molecule.

(4) Detection Kit

A detection kit according to the present invention is characterized in that it includes the wheat allergen-binding nucleic acid molecule of the present invention. It is only required that the detection kit of the present invention includes the nucleic acid molecule of the present invention, and other configurations are by no means limited. With the use of the detection kit of the present invention, it is possible to perform detection etc. of a wheat allergen as described above, for example.

The detection kit of the present invention may include the sensor of the present invention as the nucleic acid molecule of the present invention, for example. The detection kit of the present invention further may include any component in addition to the nucleic acid molecule of the present invention, for example. Examples of the component include the above-described carrier, the above-described porphyrin, a buffer solution, and instructions for use.

EXAMPLES

Next, examples of the present invention will be described. It is to be noted, however, that the present invention is by no means limited by the following examples. Commercially available reagents in the examples were used in accordance with their protocols, unless otherwise stated.

Example 1

The present example examined the binding ability and a kinetic parameter of each of the following aptamers to a wheat allergen.

(1) Aptamers

As aptamers of the present example, the following polynucleotides were synthesized.

TABLE 2

| |
| --- |
| Aptamer 1 (SEQ ID No: 1) <br> GAGGTTGGGTGGGGGAGGCAGCATGCGGGA |
| Aptamer 2 (SEQ ID No: 2) <br> GAGGTTGGGTGGGGGAGG |

To one end of each of the above-described aptamers, 20-mer polydeoxyadenine (poly(dA)) was added. The thus-obtained poly(dA)-added aptamers were used in SPR to be described below. The poly(dA) was added to the 5' end.

(2) Sample

Commercially available gluten from wheat (079-00572/Gluten, from wheat, Wako Pure Chemical Industries, Ltd.) was used as a sample in a test to be described below.

(3) Analysis of Binding Ability by SPR

The analysis of the binding ability was carried out using a ProteON XPR36 (BioRad) in accordance with its instructions for use.

First, as a sensor chip designed specifically for the ProteON, a streptavidin-immobilized chip (ProteOn NLC Sensor Chip, BioRad) was set in the ProteON XPR36. Biotinylated poly(dT) at 5 μmol/l was injected to a flow cell of the sensor chip using ultrapure water (DDW), and the binding was allowed to proceed until the signal intensity (RU: Resonance Unit) reached about 900 RU. The biotinylated poly(dT) was prepared by biotinylating the 5' end or the 3' end of 24-mer deoxythymidine. Then, the poly(dA)-added aptamer at 1 μmol/l was injected to the flow cell of the chip using an SPR buffer at a flow rate of 25 μl/min for 80 seconds, and the binding was allowed to proceed until the signal intensity reached about 800 RU. This result, which corresponds to the signal indicating the amount of the aptamer immobilized on the sensor chip, is referred to as an "aptamer immobilization measured value (A)". Subsequently, the sample was injected using the SPR buffer at a flow rate of 50 μl/min for 120 seconds, followed by washing performed by flowing the SPR buffer under the same conditions. Signal intensity measurement was performed concurrently with the injection of the sample and the washing with the SPR buffer. This result, which corresponds to the signal indicating the amount of the binding between the aptamer and the protein, is referred to as a "protein binding measured value (B)". The concentrations of the sample were 500 nmol/l, 250 nmol/l, 125 nmol/l, and 62.5 nmol/l.

The composition of the SPR buffer was as follows: 40 mmol/l HEPES, 125 mmol/l NaCl, 5 mmol/l KCl, 1 mmol/l $MgCl_2$, and 0.01% Tween® 20. The pH of the SPR buffer was set to 7.5.

Figure 2:
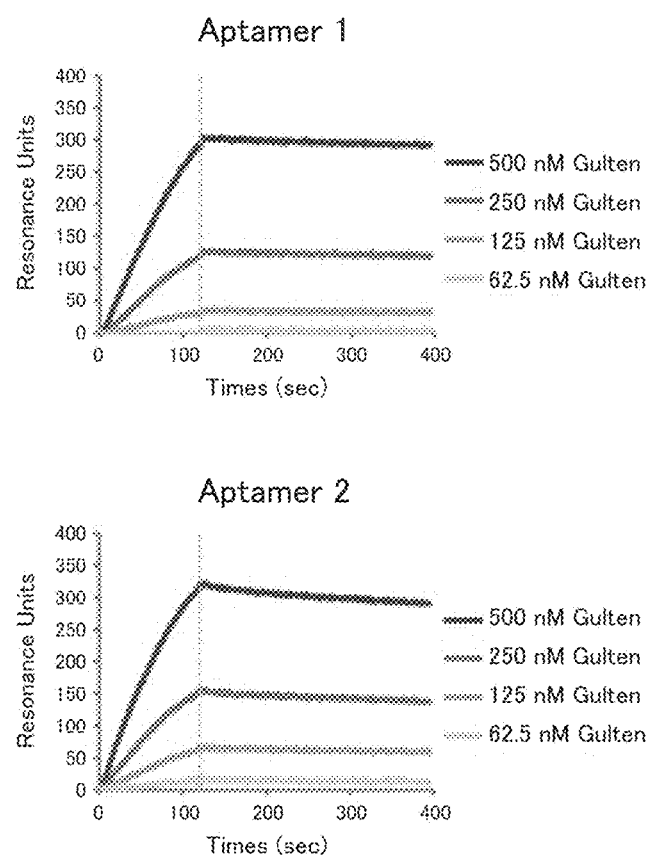
FIG. 2 shows graphs showing the binding ability of aptamers to a wheat allergen in Example 1 of the present invention.

The results thereof are shown in FIG. 2. FIG. 2 shows graphs showing the binding ability of the respective aptamers to the gluten. In FIG. 2, the horizontal axis indicates the measurement time (second), and the vertical axis indicates the signal intensity (RU). In the horizontal axis, the time from 0 to 120 seconds corresponds to the sample injection time, and the time after 120 seconds corresponds to the time for washing with the SPR buffer (the same applies hereinafter). The plotted lines in each of the graphs of FIG. 2 indicate, from the top, the results obtained when the concentration of the gluten protein was 500 nmol/l, 250 nmol/l, 125 nmol/l, and 62.5 nmol/l.

As can be seen from FIG. 2, both the aptamers exhibited binding properties to the gluten.

Also, from the results of the SPR analysis shown in FIG. 2, the kinetic parameter was calculated. The results thereof are shown in Table 3 below. As can be seen from Table 3, it was found that the dissociation constants (KD) of both the aptamers were 20 nM or less, and both the aptamers exhibited excellent binding properties to the gluten.

TABLE 3

| Aptamer | Base | KD (M) |
| --- | --- | --- |
| Aptamer 1 | 30-mer | 1. 45E-08 |
| Aptamer 2 | 18-mer | 1. 86E-08 |

While the present invention has been described above with reference to exemplary embodiments and examples, the present invention is by no means limited thereto. Various changes and modifications that may become apparent to those skilled in the art may be made in the configuration and specifics of the present invention without departing from the scope of the present invention.

INDUSTRIAL APPLICABILITY

The wheat allergen-binding nucleic acid molecule of the present invention can bind to a wheat allergen with the above-described dissociation constant. Thus, according to the wheat allergen-binding nucleic acid molecule of the present invention, a wheat allergen in a sample can be detected with high accuracy on the basis of the presence or absence of the binding with the wheat allergen, for example. Therefore, it can be said that the wheat allergen-binding nucleic acid molecule of the present invention is a very useful tool for the detection of a wheat allergen in the fields of food manufacturing, food management, food distribution, and the like, for example.

SEQUENCE LISTING 2015.11.06_TF15095WO_ST25.txt

The invention claimed is:

1. A wheat gluten-binding nucleic acid molecule comprising the following polynucleotide (a) or (b):
 (a) a polynucleotide consisting of either of sequences of SEQ ID Nos: 1 and 2;
 (b) a polynucleotide that consists of a sequence with a sequence identity of at least 80% to the sequence of SEQ ID No: 1 and comprising the sequence of SEQ ID No:2, and that binds to the wheat gluten.

2. A wheat gluten-binding nucleic acid molecule comprising the following polynucleotide (a) or (b):
 (a) a polynucleotide consisting of either of sequences of SEQ ID Nos: 1 and 2;
 (b) a polynucleotide that consists of a sequence with a sequence identity of at least 80% to the sequence of SEQ ID No: 1 and comprising the sequence of SEQ ID No:2, and that binds to the wheat gluten, wherein the polynucleotide is a DNA.

3. A wheat gluten analysis sensor comprising:
 the wheat gluten-binding nucleic acid molecule according to claim 1.

4. The wheat gluten analysis sensor according to claim 3, further comprising a nucleic acid molecule that forms a G-quartet structure.

5. The wheat gluten analysis sensor according to claim 4, wherein
 the nucleic acid molecule that forms a G-quartet structure is a DNAzyme or an RNAzyme.

6. The wheat gluten analysis sensor according to claim 3, further comprising porphyrin.

7. A wheat gluten analysis method comprising the step of:
 detecting a wheat gluten as a wheat allergen in a sample by causing the sample and the wheat gluten-binding nucleic acid molecule according to claim 1 to come into contact with each other to bind the wheat gluten in the sample and the nucleic acid molecule.

8. The wheat gluten analysis method according to claim 7, wherein the sample is at least one selected from the group consisting of foods, food ingredients, and food additives.

* * * * *